United States Patent
Lee

(10) Patent No.: US 12,429,711 B2
(45) Date of Patent: Sep. 30, 2025

(54) OPHTHALMIC DEVICE WITH BUILT-IN SELF-TEST CIRCUITRY FOR TESTING AN ADJUSTABLE LENS

(71) Applicant: Verily Life Sciences LLC, Dallas, TX (US)

(72) Inventor: Shungneng Lee, Sunnyvale, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1033 days.

(21) Appl. No.: 16/935,609

(22) Filed: Jul. 22, 2020

(65) Prior Publication Data

US 2020/0348537 A1     Nov. 5, 2020

Related U.S. Application Data

(62) Division of application No. 15/900,200, filed on Feb. 20, 2018, now Pat. No. 10,761,347.

(Continued)

(51) Int. Cl.
*G02C 7/04*        (2006.01)
*A61F 2/16*       (2006.01)
(Continued)

(52) U.S. Cl.
CPC .............. *G02C 7/04* (2013.01); *A61F 2/1624* (2013.01); *A61F 2/1627* (2013.01); *G02C 7/08* (2013.01);
(Continued)

(58) Field of Classification Search
CPC . G02C 7/04; G02C 7/08; G02C 7/081; G02C 7/083; G02C 7/085; G02C 2202/16;
(Continued)

(56) References Cited

U.S. PATENT DOCUMENTS 3,046,418 A * 7/1962 Eachus .................. G01R 27/02
                                                              361/188
3,676,770 A * 7/1972 Sharaf .................. G01R 27/205
                                                              320/136

(Continued)

FOREIGN PATENT DOCUMENTS

AU       2013201684 B2    8/2014
EP         2988363 A1     2/2016
(Continued)

OTHER PUBLICATIONS

International Search Report and Written Opinion from the International Searching Authority mailed Jun. 15, 2018, for International Application No. PCT/US2018/023637, filed Mar. 21, 2018, 14 pages.

*Primary Examiner* — Travis S Fissel
*Assistant Examiner* — Daniel J. Jordan
(74) *Attorney, Agent, or Firm* — Christensen O'Connor Johnson Kindness PLLC

(57) ABSTRACT

An ophthalmic device includes an enclosure that is compatible for wearing in or on an eye. An adjustable lens is disposed within the enclosure. Driver circuitry is disposed within the enclosure and coupled to drive the adjustable lens and change its optical power. Built-in-self-test (BIST) circuitry is disposed within the enclosure and coupled to the adjustable lens. The BIST circuitry includes an impedance measurement circuit coupled to selectively measure an impedance of the adjustable lens. A controller is disposed within the enclosure and includes BIST control logic that measures the impedance of the adjustable lens with the impedance measurement circuit to determine a health status of the adjustable lens.

20 Claims, 10 Drawing Sheets

Related U.S. Application Data

(60) Provisional application No. 62/475,545, filed on Mar. 23, 2017.

(51) Int. Cl.
*A61F 2/48* (2006.01)
*G02C 7/08* (2006.01)

(52) U.S. Cl.
CPC ............ *G02C 7/081* (2013.01); *A61F 2/1648* (2013.01); *A61F 2/482* (2021.08); *A61F 2210/0076* (2013.01); *A61F 2240/008* (2013.01); *G02C 7/083* (2013.01); *G02C 7/085* (2013.01); *G02C 2202/16* (2013.01); *G02C 2202/18* (2013.01)

(58) Field of Classification Search
CPC .. G02C 2202/18; A61F 2/1624; A61F 2/1627; A61F 2/1648; A61F 2/482; A61F 2210/0076; A61F 2240/008; G01R 27/02; G01R 31/2836; G01R 27/00; G02B 1/043
USPC ............... 351/159.01, 159.02, 159.24, 159.3
See application file for complete search history.

(56) References Cited

U.S. PATENT DOCUMENTS

| | | | | |
|---|---|---|---|---|
| 3,983,338 | A * | 9/1976 | Mathauser | H04M 3/301 379/422 |
| 4,795,248 | A * | 1/1989 | Okada | G02C 7/083 351/158 |
| 9,308,348 | B2 * | 4/2016 | Mulvihill | A61M 25/0113 |
| 9,541,772 | B2 | 1/2017 | De Sio et al. | |
| 10,702,375 | B2 * | 7/2020 | Roholt | A61F 2/1635 |
| 2005/0264314 | A1 | 12/2005 | Gearhardt | |
| 2009/0125079 | A1 * | 5/2009 | Armstrong | A61N 1/3605 607/45 |
| 2009/0201242 | A1 * | 8/2009 | Govil | G09G 3/346 345/98 |
| 2011/0260746 | A1 | 10/2011 | Huang et al. | |
| 2012/0245444 | A1 | 9/2012 | Otis et al. | |
| 2013/0218270 | A1 | 8/2013 | Blanckaert et al. | |
| 2014/0085602 | A1 | 3/2014 | Ho et al. | |
| 2014/0343387 | A1 * | 11/2014 | Pugh | A61B 5/6821 600/365 |
| 2015/0362751 | A1 * | 12/2015 | Biederman | H02J 7/0068 349/13 |
| 2015/0362755 | A1 * | 12/2015 | Lee | G02C 7/04 351/159.73 |
| 2015/0364822 | A1 * | 12/2015 | O'Driscoll | H01Q 7/005 343/718 |
| 2016/0324628 | A1 | 11/2016 | Gupta et al. | |

FOREIGN PATENT DOCUMENTS

JP       H0562876 U  *  8/1993
WO      2008039242 A1    4/2008

* cited by examiner

RPAR & CPAR MEASUREMENT CIRCUIT

OPHTHALMIC DEVICE WITH BUILT-IN SELF-TEST CIRCUITRY FOR TESTING AN ADJUSTABLE LENS

CROSS-REFERENCE TO RELATED APPLICATIONS

This application is a divisional of U.S. application Ser. No. 15/900,200 filed Feb. 20, 2018, which claims the benefit of U.S. Provisional Application No. 62/475,545, filed Mar. 23, 2017, both of which are hereby incorporated by reference.

TECHNICAL FIELD

This disclosure relates generally to ophthalmic lenses, and in particular but not exclusively, relates to testing ophthalmic lenses.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that changes the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide (110 million in the United States alone) and that number is expected to rise as the world's population ages. Techniques and devices that can help individuals offset the effects of Presbyopia are increasingly in demand.

Smart ophthalmic devices can aid a user with accommodation to counter the age-related effects of presbyopia. However, such smart ophthalmic devices have optical components that should be tested to validate their correct manufacture, assembly, and operation. Conventional techniques for testing the optics of an ophthalmic device use external optical equipment, such as optical coherence tomography equipment or custom camera solutions, to measure the optics. This external test equipment is both costly and overly time consuming for large scale manufacture.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of apparatus, system, and method of operation for self-testing the health status of an adjustable lens of an ophthalmic device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
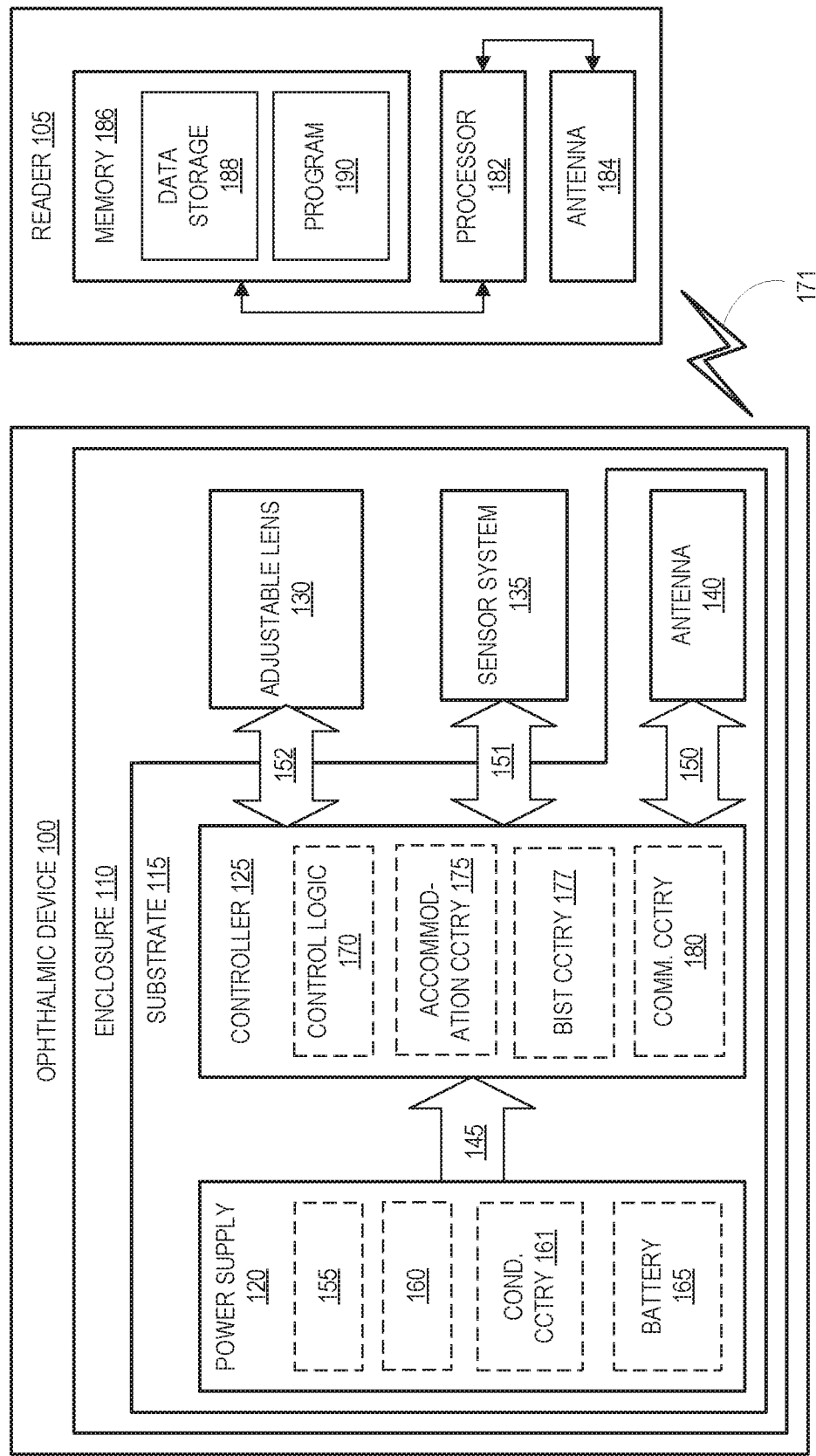
FIG. 1 is a functional block diagram of an ophthalmic device with built-in self-test ("BIST") circuitry for testing and monitoring the health status of an adjustable lens for accommodation, in accordance with an embodiment of the disclosure.

FIG. 1 is a functional block diagram of an ophthalmic device 100 with built-in self-test ("BIST") circuitry for testing and monitoring the health status of an adjustable lens, in accordance with an embodiment of the disclosure. In the illustrated embodiment, ophthalmic device 100 includes an enclosure 110 formed to be compatible for wearing in or on an eye of a user. For example, ophthalmic device 100 may be contact-mounted to a corneal surface of an eye or implanted into the interior of the eye (e.g., anterior or posterior chambers). A substrate 115 is embedded within or surrounded by enclosure 110 to provide a mounting surface for a power supply 120, a controller 125, an antenna 140, and various interconnects 145, 150, 151, and 152. An adjustable lens 130 and sensor system 135 are also included within enclosure 110 to provide adjustable optical power for auto-accommodation.

The illustrated embodiment of power supply 120 includes an energy harvesting antenna 155, charging circuitry 160, conditioning circuitry 161 (e.g., capacitor), and a battery 165. The illustrated embodiment of controller 125 includes control logic 170, accommodation circuitry 175, built-in self-test (BIST) circuitry 177, and communication circuitry 180. Because ophthalmic device 100 includes electronics to provide auto-accommodation by varying the optical power of adjustable lens 130, it may also be referred to as a smart contact lens or smart intraocular lens (IOL) depending upon the particular implementation and form factor. In a smart contact lens implementation, enclosure 110 is configured to be removeably mounted over a cornea of a user's eye, and has a size and shape that permits eyelid motion when enclosure 110 is so mounted.

Sensor system 135 may be implemented using a variety of different sensor systems capable of measuring an environment of ophthalmic device 100 for gaze detection or focal distance determination. If accommodation circuitry 175 in conjunction with sensor system 135 can determine where the user is looking, the optical power of adjustable lens 130 can be adjusted to assist the user's accommodation and enhance what the user sees. In one embodiment, sensor system 135 is a tear-film-sensitive sensors system disposed to measure an impedance of a tear-film in an eye of the user, and to output a signal indicative of this impedance. For example, one or more tear-film-sensitive sensors can measure the impedance across a surface of ophthalmic device 100, which is correlated with a location of ophthalmic device 100 in the eye of the user and a direction of the user's vision. Since the impedance of the user's tear-film can be correlated to a gaze direction, feedback from sensor system 135 can be used by accommodation circuitry 175 to adjust the optical power of adjustable lens 130.

In other contact lens embodiments, sensor system 135 may be implemented using photo-detectors or even capacitive sensors which measure eyelid overlap and generate output signals that correlate to gaze direction. In IOL embodiments, sensor system 135 may including mechanical, electromechanical, or electrical sensors that measure a user's ciliary muscle to determine a desired level of accommodation. Other sensor system and techniques for determining the amount of accommodation to be provided by adjustable lens 130 may be implemented.

Adjustable lens 130 may be implemented using different adjustable lens technologies. In one embodiment, adjustable lens 130 is liquid crystal material disposed in a curved lens structure. The application of a bias signal across the liquid crystal material changes its refractive index, which changes the optical power of the overall lens structure. In another embodiment, adjustable lens 130 is an electrowetting lens. An example electrowetting lens includes the electrostatic manipulation of the shape of a boundary between two immiscible fluids each having different refractive indexes to change an optical power of the lens. In yet another embodiment, adjustable lens 130 may be implemented using a microelectromechanical system (MEMS).

In the illustrated embodiment, antenna 140, controller 125, and power supply 120 are disposed on substrate 115, while sensor system 135 and adjustable lens 130 are disposed in enclosure 110, but not on substrate 115. However, in other embodiments, the various components contained in ophthalmic device 100 may be disposed on or off substrate 115 depending on the specific design. For example, in one embodiment, sensor system 135 may also be disposed on substrate 115.

Substrate 115 includes one or more surfaces suitable for mounting controller 125, power supply 120, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. Substrate 115 can be a relatively rigid material, such as polyethylene terephthalate ("PET") or another material sufficient to structurally support the circuitry and/or electronics within enclosure 110. Ophthalmic device 100 can alternatively be arranged with a group of unconnected substrates rather than a single substrate 115. For example, controller 125 and power supply 120 can be mounted to one substrate 115, while antenna 140 is mounted to another substrate 115 and the two can be electrically connected via interconnect 150. In one embodiment, substrate 115 is shaped as a ring or flattened ring with a radial width dimension sufficient to provide a mounting platform for the embedded electronic components.

In the illustrated embodiment, power supply 120 includes a battery 165 to power the various embedded electronics, including controller 125. Battery 165 may be inductively charged by charging circuitry 160 (e.g., rectifier, regulator, etc.) and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Additionally or alternatively, power supply 120 may include a photovoltaic cell or inertial power scavenging system. In one embodiment, conditioning circuitry 161 is a capacitor that filters or conditions the output of battery 165.

Controller 125 contains logic to choreograph the operation of the other embedded components. Control logic 170 controls the general operation of ophthalmic device 100, including providing a logical user interface, power control functionality, etc. Accommodation circuitry 175 includes logic for receiving feedback signals from sensors monitoring the orientation of the eye, determining the current gaze direction or focal distance of the user (e.g., via sensor system 135), and manipulating the optical power of adjustable lens 130 in response. In one embodiment, accommodation circuitry 175 further includes signal driver circuitry for driving a voltage or current onto drive terminals of adjustable lens 130. This auto-accommodation can be implemented in real-time based upon feedback from sensor system 135, or permit the user to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The operation of BIST circuitry 177 is described in further detail below. The various logic modules of controller 125 may be implemented in software/firmware executed on a general purpose microprocessor, in hardware (e.g., application specific integrated circuit), or a combination of both.

The illustrated embodiment also includes reader 105 with a processor 182, an antenna 184, and memory 186. Memory 186 in reader 105 includes data storage 188 and program instructions 190. As shown reader 105 may be disposed outside of ophthalmic device 100, but may be placed in its proximity to charge ophthalmic device 100, send instructions to ophthalmic device 100, and/or extract data from ophthalmic device 100. In one embodiment, reader 105 may resemble a conventional contact lens holder that the user places ophthalmic device 100 in at night to charge, extract data, clean the lens, etc.

External reader 105 includes an antenna 184 (or group of more than one antennae) to send and receive wireless signals 171 to and from eye-mountable device 100. External reader 105 also includes a computing system with a processor 182 in communication with a memory 186. Memory 186 can include a data storage 188 to store data, such as data logs (e.g., user logs), program settings (e.g., to adjust behavior of ophthalmic device 100 and/or external reader 105), etc. Memory 186 can also include program instructions 190 for execution by processor 182. For example, program instructions 190 can cause external reader 105 to provide a user interface that allows for retrieving information communicated from ophthalmic device 100 or allows transmitting information to ophthalmic device 100 to program or otherwise select operational modes of ophthalmic device 100.

External reader 105 can be a smart phone, digital assistant, or other portable computing device with wireless connectivity sufficient to provide the wireless communication link 171. External reader 105 can also be implemented as an antenna module that can be plugged in to a portable computing device, such as in an embodiment where the communication link 171 operates at carrier frequencies not commonly employed in portable computing devices. In some instances, external reader 105 is a special-purpose device configured to be worn relatively near a wearer's eye to allow the wireless communication link 171 to operate with a low power budget. For example, the external reader 105 can be integrated in a piece of jewelry such as a necklace, earing, etc. or integrated in an article of clothing worn near the head, such as a hat, headband, etc.

Figure 2:
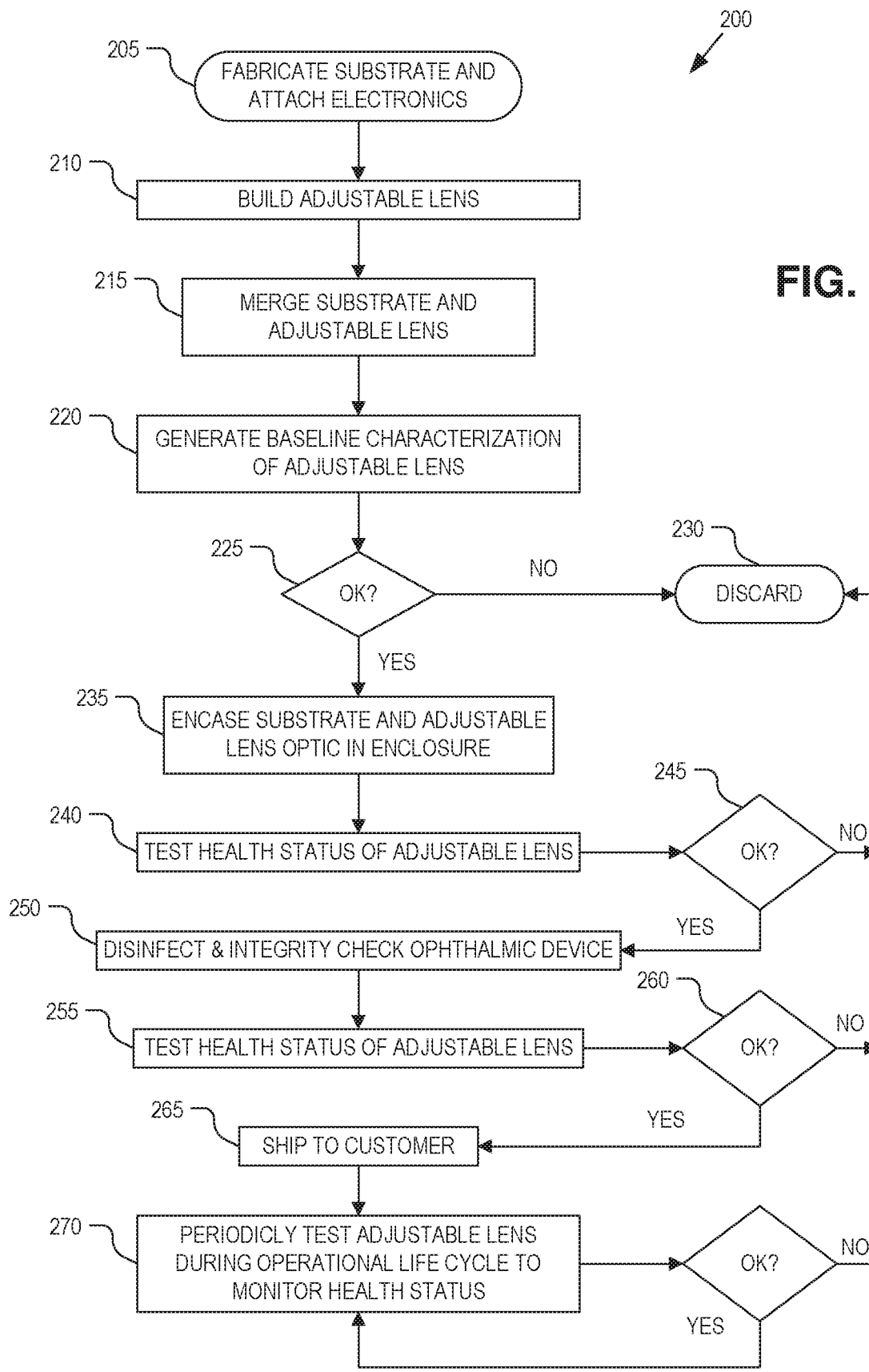
FIG. 2 is a flow chart illustrating how BIST circuitry can be used to both test the proper manufacture/assembly of the adjustable lens and monitor the adjustable lens throughout an operational life cycle of the ophthalmic device, in accordance with an embodiment of the disclosure.

FIG. 2 is a flow chart 200 illustrating how BIST circuitry 177 can be used to both test the proper manufacture/assembly of adjustable lens 130 and monitor adjustable lens 130 throughout an operational life cycle of ophthalmic device 100, in accordance with embodiments of the disclosure. As ophthalmic device 100 is manufactured, it is desirable to regularly validate or test its components throughout the manufacture flow to identify defects as early as possible. If defects can be identified early in the fabrication pipeline, and the defective item discarded or fixed, valuable manufacturing resources will not be consumed by defective items. While quick electrical checks can be performed with probes and/or wireless communications that run diagnostic routines, measuring and determining the health status of adjustable lens 130 is a time-consuming task when using conventional techniques. These techniques use expensive external optical test equipment (e.g., cameras, coherent tomography equipment, etc.) to capture and measure diopter changes in the optical properties of adjustable lens 130 and use these measurements to determine a health status (e.g., functioning within acceptable parameters or defective) of the optics. Since these external optical tests are time consuming, large volume manufacture of ophthalmic devices has historically only used statistical batch testing—not per item testing. Furthermore, given the cost and complexity of this optical test equipment, in-field or operational life cycle testing of ophthalmic devices is not realistic for the end user.

In contrast, FIG. 2 illustrates an example assembly flow and life cycle use that incorporate regular or periodic testing of adjustable lens 130 to determine its health status so that a defective or near defective instances of ophthalmic device 100 can be quickly identified and cutoff from consuming further resources in manufacture or discarded/replaced before in-use failure.

In process block 205, the embedded electronics (e.g., power supply 120, controller 125, antenna 140) are fabricated and assembled onto substrate 115. Similarly, in process block 210, adjustable lens 130 is assembled. In process block 215, adjustable lens 130 and substrate 115 with its embedded electronics merged into a single unit that is at least partially operational. In process block 220, reader 105 activates BIST circuitry 177 to perform an initial measurement test on adjustable lens 130. This initial measurement measures electrical properties of adjustable lens 130, such as parallel resistance and parallel capacitance, to obtain a baseline characterization of adjustable lens 130.

Parallel resistance and parallel capacitance, as measured across the terminals of adjustable lens 130 (e.g., drive terminals for actuating adjustable lens 130), can be correlated to a health status of adjustable lens 130. Accordingly, if either or both of the measured parallel resistance (Rpar) or parallel capacitance (Cpar) are found to be outside expected resistance or capacitance ranges, then the adjustable lens 130 may be determined to be defective (decision block 225) and therefore the particular instance of ophthalmic device 100 discarded (process block 230). The measurement of Rpar and Cpar values may even be used to infer absolute diopter values and/or diopter changes both during manufacture and during in-field use.

On the other hand, if both of the measured Rpar and Cpar values are found to be within expected resistance or capacitance ranges, then manufacture continues to process block 235. The baseline characterization determined in process block 220 may also be saved (e.g., within controller 125) for future comparisons to monitor changes in Rpar and Cpar during fabrication and ultimately during the operational life cycle of the particular ophthalmic device 100. Incremental changes in Rpar and Cpar may also be used to estimate health status or estimate remaining life span.

In process block 235, the merged substrate 115 and adjustable lens 130 module is over-molded or otherwise encased within enclosure 110. Again reader 105 can activate BIST circuitry 177 to perform another health status test on adjustable lens 130 (process block 240) to check whether adjustable lens 130 was damaged during the over-molding. If Rpar and Cpar test outside of expected ranges or deviate more than a threshold amount from their baseline characterizations, then the health status of ophthalmic device 100 may be deemed defective (decision block 245) and discarded (process block 230). Otherwise, manufacture continues to disinfection and integrity checking (process block 250). Integrity checking may include a liquid infiltration test to ensure ophthalmic device 100 is properly sealed. Again, another health status check can be performed at process block 255 to validate that the disinfection and integrity check did not damage adjustable lens 130. If the health status check is passed (decision block 260), then the finished product is shipped to a customer (process block 265), where ophthalmic device 100 enters its operational life cycle.

Once in operational use, BIST circuitry 177 can continue to perform periodic checks to monitor the health status of adjustable lens 130 (process block 270). These periodic checks during the operational life cycle of ophthalmic device 100 reduce the likelihood of an unexpected failure while in use. If the measured impedance of adjustable lens 130 degrades at a faster than expected rate, the user can be instructed to discard ophthalmic device 100 prior to catastrophic failure. In one embodiment, the health status checks performed in process block 270 are executed nightly (or other regularly scheduled time) when ophthalmic device 100 is not being used. In one embodiment, the health status checks performed in process block 270 may be performed while ophthalmic device 130 is disposed in or on the user's eye, since test results may be communicated wirelessly to reader 105. In yet another embodiment, health status checks may also be initiated by reader 105 as an on-demand test.

Figure 3:
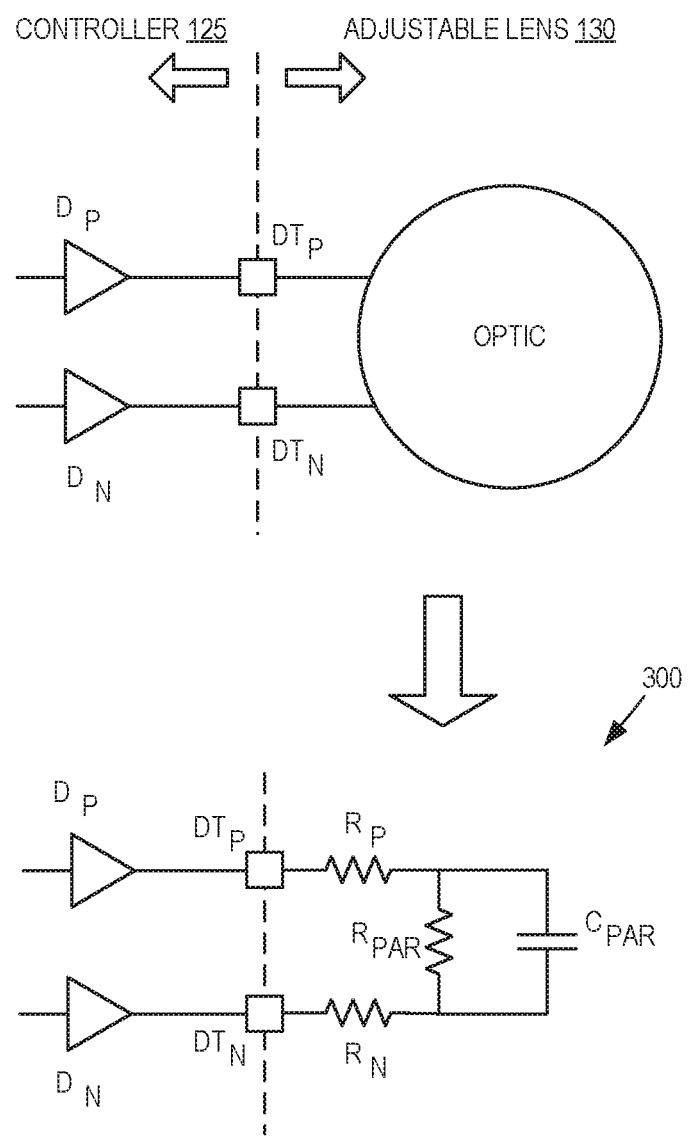
FIG. 3 illustrates how the impedance of an adjustable lens of an ophthalmic device can be represented with a circuit diagram including a parallel resistance and a parallel capacitance, in accordance with an embodiment of the disclosure.

FIG. 3 illustrates how the impedance of adjustable lens 130 of ophthalmic device 100 can be depicted with a circuit representation 300, in accordance with an embodiment of the disclosure. As illustrated, controller 125 includes accommodation drivers Dp and Dn (i.e., driver circuitry) that drive adjustable lens 130 through drive terminals DTp and DTn. In the illustrated embodiment, adjustable lens 130 includes both the optic that provides the adjustable optical power and the drive terminals DTp and DTn, which are electrodes that couple to the optic for applying drive signals across the optic. Adjustable lens 130 may be implemented as a liquid crystal cell, an electrowetting lens, a MEMS lens, or otherwise. Drive terminals DTp and DTn may be implemented using a variety of electrode materials as such indium-tin-oxide (ITO), sliver nanowires, gold, conductive epoxy, or otherwise.

Circuit representation 300 includes a parallel capacitance Cpar, a parallel resistance Rpar, and terminal resistances Rp and Rn. Cpar and Rpar represent the parallel capacitance and parallel resistance, respectively, of the optic of adjustable lens 130. Terminal resistances Rp and Rn are serial resistances of the drive terminals DTp and DTn. Rp and Rn are dependent upon the material choice and physical form factors of drive terminals DTp and DTn. As such, Rp and Rn are known, fixed values, which can be subtracted from the measured resistance across DTp and DTn when determining Rpar. Rp and Rn are typically insensitive to applied voltage/current to drive terminals DTp and DTn. In contrast, Cpar may change based upon applied voltage/current to DTp and DTn. Similarly, Rpar may be sensitive to applied voltage/current to drive terminals DTp and DTn, but similar to Cpar, an overall average/estimate is made during measurement.

Typically, Rpar is greater than 100 megaohms for low power operation of adjustable lens 130, though over values may be possible depending upon the implementation of the optic. If Rpar is too great, then an open circuit condition may have occurred (e.g., a drive terminal/electrode has separated from the optic, optic itself has failed, etc.). If Rpar is too low, then a short circuit or low resistance condition may have occurred, which can also indicate a failure. Accordingly, if Rpar measures outside of an expected resistance range, then adjustable lens 130 may be deemed to be defective. However, if Cpar measures outside of an expected capacitance range, adjustable lens 130 may also be deemed defective. These expected resistance and capacitance ranges may change overtime during the operational life cycle of ophthalmic device 100. Since Rpar and Cpar may not be static values as adjustable lens 130 ages, the magnitude of change, or even the rate of change, of Rpar or Cpar may be monitored overtime and these changing values used to determine the health status of adjustable lens 130.

Figure 4:
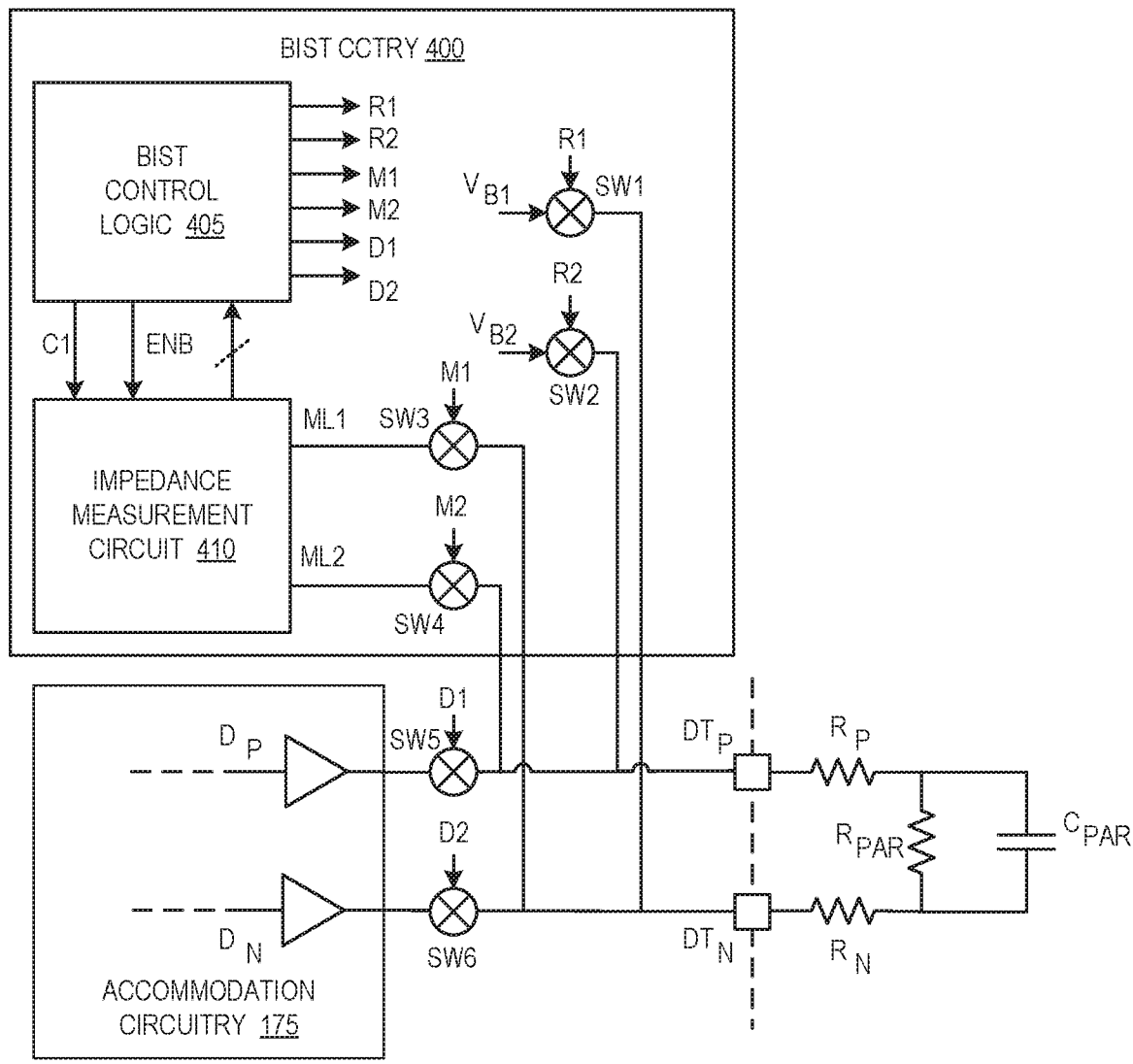
FIG. 4 illustrates functional components of BIST circuitry for testing the health status of an adjustable lens, in accordance with an embodiment of the disclosure.

FIG. 4 illustrates functional components of BIST circuitry 400 for testing the health status of adjustable lens 130, in accordance with an embodiment of the disclosure. BIST circuitry 400 is one possible implementation of BIST circuitry 177 illustrated in FIG. 1. The illustrated embodiment of BIST circuitry 400 includes BIST control logic 405, an impedance measurement circuit 410, and switches SW1-SW4. Switches SW5 and SW6 selectively couple accommodations drivers Dp and Dn to drive terminals DTp and DTn. While switches SW5 and SW6 are logically illustrated as external components of BIST circuitry 400, these switches could be considered as part of BIST circuitry 400.

BIST control logic 400 includes logic that choreographs the operation of the other components of BIST circuitry 400 for the purpose of measuring and/or monitoring the health status of adjustable lens 130. In one embodiment, BIST control logic 400 is implemented as software/firmware instructions that are executed by a microcontroller. In another embodiment, BIST control logic 400 is hardware logic (e.g., application specific integrated circuit, field programmable gate array, logic gates, etc.). In yet other embodiments, BIST control logic 400 is implemented as a combination of software/firmware instructions and hardware logic.

Impedance measurement circuit 410 is a circuit capable of measuring the impedance of adjustable lens 130 under the direction of BIST control logic 405. In one embodiment, impedance measurement circuit 410 is a resistance measurement circuit. In one embodiment, impedance measurement circuit 410 is a reactance measurement circuit (e.g., capable of measuring inductance or capacitance). In one embodiment, impedance measurement circuit 410 is a capacitance measurement circuit. In one embodiment, impedance measurement circuit 410 is both a resistance measurement circuit and a capacitance measurement circuit.

Figure 5:
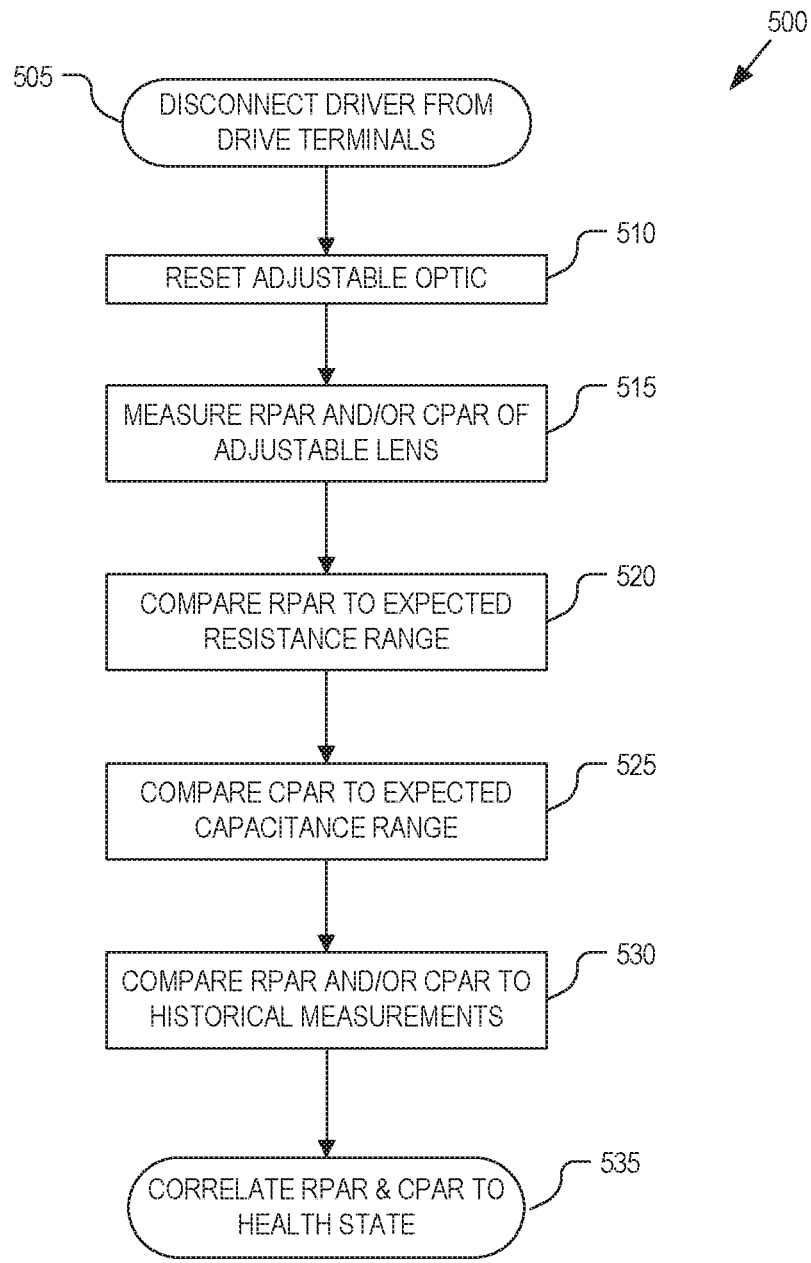
FIG. 5 is a flow chart illustrating a process of operation of BIST circuitry while testing and monitoring the health status of an adjustable lens of an ophthalmic device, in accordance with an embodiment of the disclosure.

FIG. 5 is a flow chart illustrating a process 500 of operation of BIST circuitry 400 while testing and monitoring the health status of adjustable lens 130, in accordance with an embodiment of the disclosure. Process 500 is described with reference to FIG. 4. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In a process block 505, accommodation drivers Dp and Dn are disconnected from drive terminals DTp and DTn. In FIG. 4, switches SW5 and SW6 are open circuited via control signals D1 and D2. In a process block 510, adjustable lens 130 is reset to a known state. In the embodiment illustrated in FIG. 4, adjustable lens 130 is reset by closing switches SW1 and SW2 to apply bias voltages VB1 and VB2 to drive terminals DTn and DTp. In one embodiment, VB1 and VB2 are ground voltages. In other embodiments, a default voltage may be applied across drive terminals DTn and DTp. After initially resetting the potentials on drive terminals DTn and DTp, at least switch SW1 is open circuited.

In a process block 515, one or both of switches SW3 and SW4 are closed circuited to connect impedance measurement circuit 410 to adjustable lens 130 in preparation for measuring Rpar and/or Cpar. Once a resistance value indicative of Rpar is acquired by impedance measurement circuit 410, it is compared against an expected resistance range by BIST control logic 405 (process block 520). Once a capacitance value indicative of Cpar is acquired by impedance measurement circuit 410, it is compared against an expected capacitance range by BIST control logic 405 (process block 525). In a process block 530, the measured values for one or both of Rpar and Cpar are compared to previous or historical measurements to monitor changes in these values.

Finally, in a process block 535, the measurements/changes in Rpar and/or Cpar are correlated to a health status of adjustable lens 130. For example, if the measured resistance value falls outside an expected resistance range, then the health status of adjustable lens 130 may be deemed defective. Similarly, if the measured capacitance value falls outside an expected capacitance range, then the health status of adjustable lens 130 may also be deemed to be defective. The magnitude or rate of changes in the measured values for Rpar and/or Cpar may be tracked over time and also correlated to a health status of adjustable lens 130. For example, while the measured values of Rpar and Cpar are within expected ranges, if the rate of change is great than to be expected, then the health status may be deemed defective. On the other hand, if the Rpar and Cpar are within expected ranges, then the health status may be deemed acceptable or functional. Similarly, if the rate or magnitude of changes in Rpar and Cpar are within expected ranges, then the health status may be deemed acceptable or functional. In one embodiment, an estimated remaining life span for ophthalmic device 100 is calculated based at least in part upon the changes or the rate of changes in Rpar or Cpar.

Figure 6A:
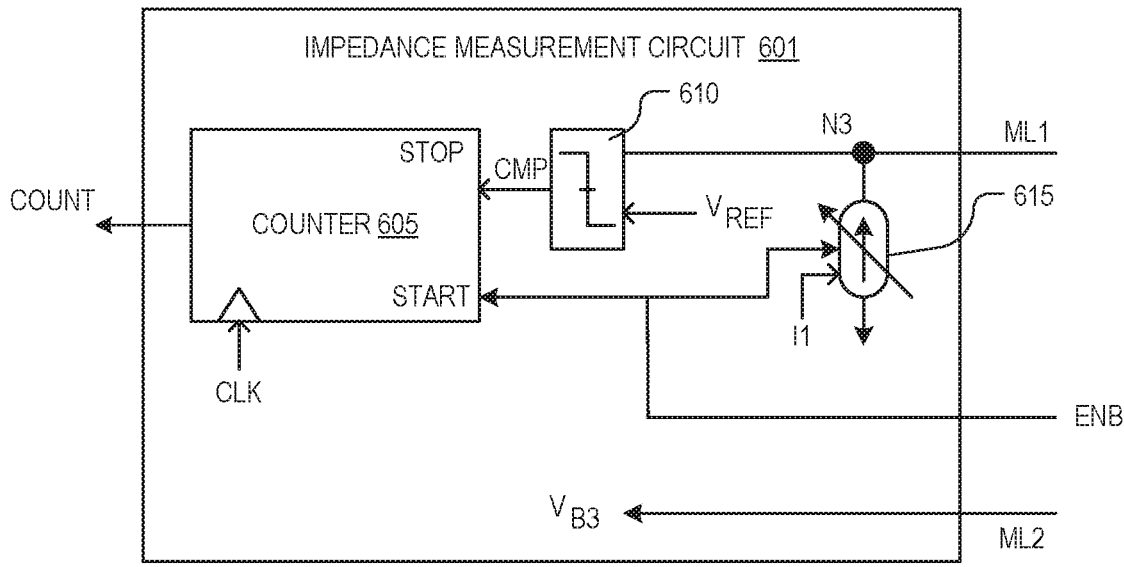
FIG. 6A is a functional block diagram illustrating an impedance measurement circuit for testing parallel capacitance of an adjustable lens, in accordance with an embodiment of the disclosure.

FIG. 6A is a functional block diagram illustrating an impedance measurement circuit 601 for testing parallel capacitance of adjustable lens 130, in accordance with an embodiment of the disclosure. Impedance measurement circuit 601 is one possible implementation of impedance measurement circuit 410 illustrated in FIG. 4. The illustrated embodiment of impedance measurement circuit 601 includes a counter 605, a voltage comparator 610, and a current source 615.

Comparator 610 has two inputs coupled to compare the voltage at circuit node N3 to a reference voltage Vref and generates a compare value CMP on its output. The output compare value CMP is coupled to the STOP input of counter 605 to selectively stop counter 605 when the voltage at circuit node N3 equals Vref. Circuit node N3 is selectively coupled via measure line ML1 and switch SW3 to drive terminal DTn when BIST circuitry 400 is in a test mode.

Current source 615 is coupled to drive current onto adjustable lens 130 through drive terminal DTn via the measure line ML1 and switch SW3. During operation, BIST control logic 405 enables current source 615 and counter 605 at the same time via assertion of the enable signal ENB. Current source 615 begins to charge the capacitance Cpar of adjustable lens 130 at a rate dependent upon the charge current output by current source 615. As Cpar is charged, the voltage at circuit node N3 rises until it reaches Vref, at which time voltage comparator 610 toggles its output CMP and counter 605 stops counting. The count value of counter 605 is then output to BIST control logic 405 for correlating to a capacitance value for Cpar. Since the rise time and the charging current are known or measured values, Cpar can be determined. In one embodiment, current source 615 is a variable current source with a selectable output current that is selected by BIST control logic 405 via appropriate assertion of control signal I1. In one embodiment, impedance measurement circuitry 601 further includes a voltage source to output a bias voltage VB3 on measurement line ML2 for resetting the voltage potential on drive terminal DTp via selective activation of switch SW4 under the control of BIST control logic 405.

Figure 6B:
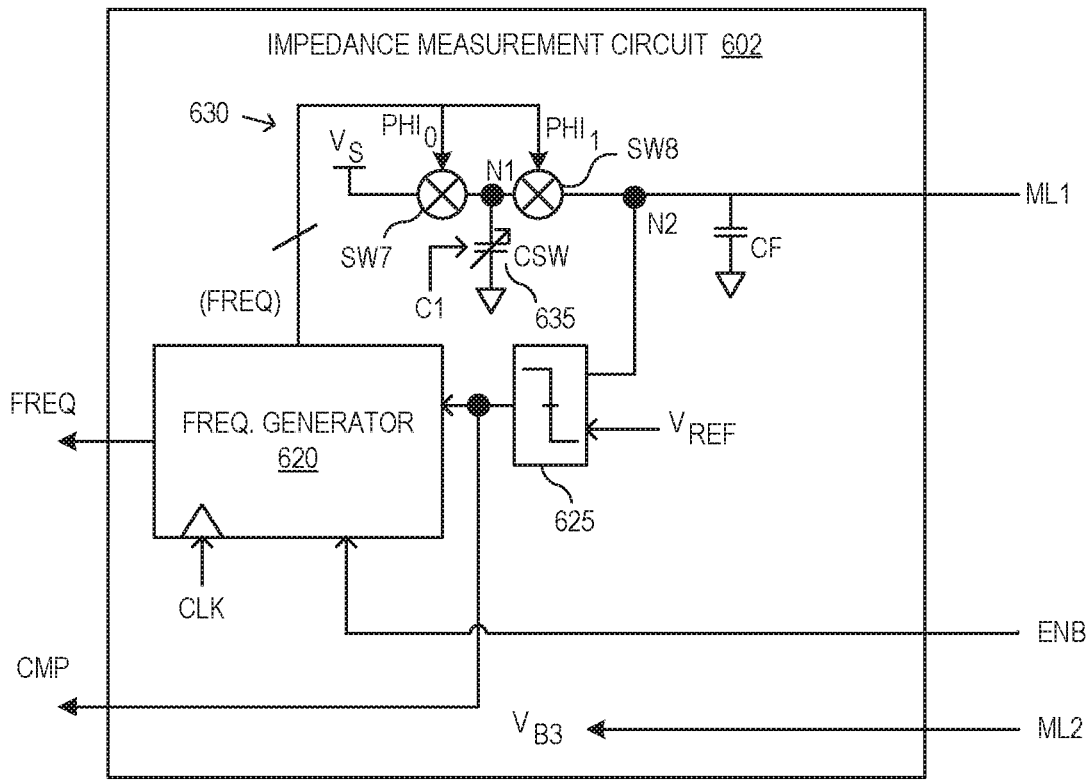
FIG. 6B is a functional block diagram illustrating an impedance measurement circuit for testing parallel resistance of an adjustable lens, in accordance with an embodiment of the disclosure.

FIG. 6B is a functional block diagram illustrating an impedance measurement circuit 602 for testing parallel resistance of adjustable lens 130, in accordance with an embodiment of the disclosure. Impedance measurement circuit 602 is one possible implementation of impedance measurement circuit 410 illustrated in FIG. 4. The illustrated embodiment of impedance measurement circuit 602 includes a frequency generator 620, a voltage comparator 625, a capacitive switch network 630, and a filter capacitor CF. The illustrated embodiment of capacitive switch network 630 includes switches SW7 and SW8, capacitance circuit 635 having a capacitance CSW, and voltage source Vs.

Comparator 625 has two inputs coupled to compare the voltage at circuit node N2 to a reference voltage Vref and generates a compare value CMP on its output. The output compare value CMP is coupled as a feedback signal to frequency generator 620 to control the frequency FREQ of switching signals PHI0 and PHI1 output by frequency generator 620. In one embodiment, both the frequency value FREQ and the compare signal CMP are output back to BIST control logic 405. Frequency generator 620 generates switching signals PHI0 and PHI1 to control the switching frequency of switches SW7 and SW8. In one embodiment, switching signals PHI0 and PHI1 are nonoverlapping signals that open and close SW7 and SW8, respectively, in a nonoverlapping manner at the same frequency FREQ. Capacitive switch network 630 has an effective resistance Reff that is dependent on the switching frequency FREQ and the capacitance value CSW according to equation 1, $$Reff = \frac{1}{(CSW * FREQ)}. \quad (1)$$

When BIST control logic 405 enables frequency generator 620 and connects impedance measurement circuitry 602 to drive terminal DTn via switch SW3 and measurement line ML1 (see FIG. 4), a voltage divider circuit is established between capacitive switch network 630 and Rpar of adjustable lens 130. By comparing the voltage at circuit node N2 between capacitive switch network 630 and Rpar of adjustable lens 130 to a reference voltage Vref (e.g., Vref=Vs/2), the resistance of Rpar is measured as a comparative value to the effective resistance of capacitive switch network 630.

In one embodiment, capacitive switch network 630 has a variable capacitance that is selectable by BIST control logic 405 via control signal C1. In one embodiment, impedance measurement circuitry 602 further includes a voltage source to output a bias voltage VB3 on measurement line ML2 for resetting the voltage potential on drive terminal DTp via selective activation of switch SW4 under the control of BIST control logic 405. It should be appreciated that embodiments of impedance measurement circuit 410 in FIG. 4 may include both of impedance measurement circuits 601 and 602 operating in a time sharing manner to measure both Cpar and Rpar of adjustable lens 130.

Figure 6C:
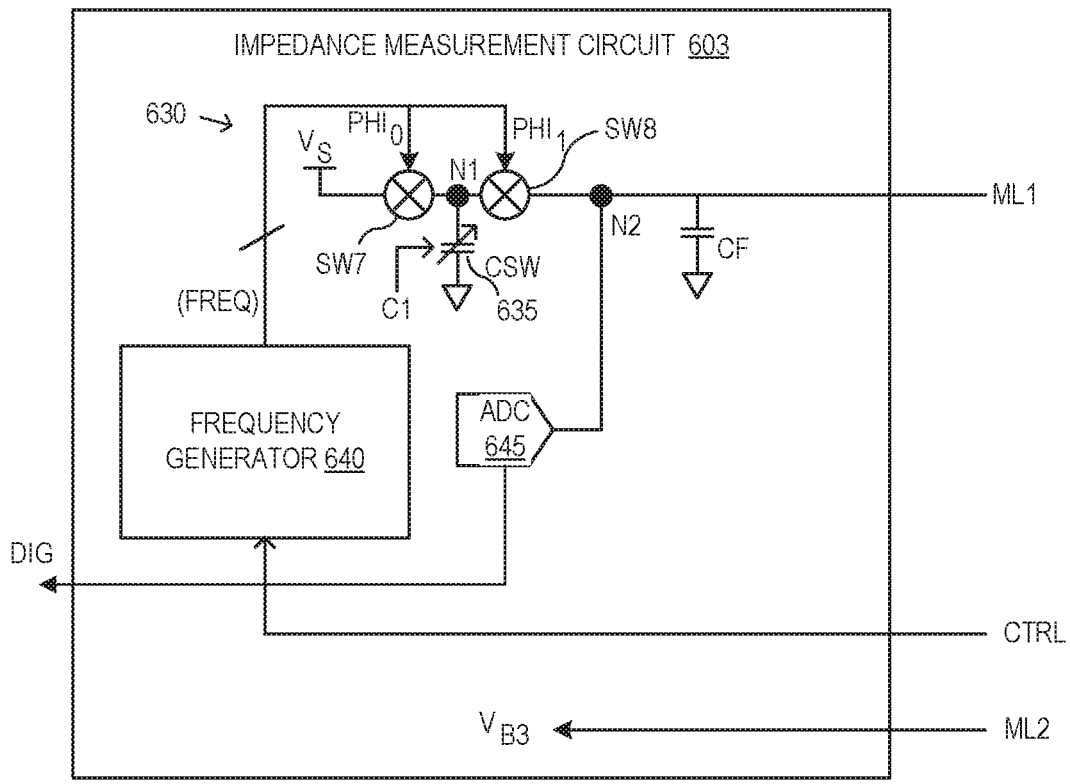
FIG. 6C is a functional block diagram illustrating an impedance measurement circuit for testing both parallel resistance and parallel capacitance of an adjustable lens, in accordance with an embodiment of the disclosure.

FIG. 6C is a functional block diagram illustrating an impedance measurement circuit 603 for testing both parallel resistance and parallel capacitance of adjustable lens 130, in accordance with an embodiment of the disclosure. Impedance measurement circuit 603 is yet another possible implementation of impedance measurement circuit 410 illustrated in FIG. 4. The illustrated embodiment of impedance measurement circuit 603 includes a frequency generator 640, an analog-to-digital converter (ADC) 645, capacitive switch network 630, and filter capacitor CF.

Figure 6D:
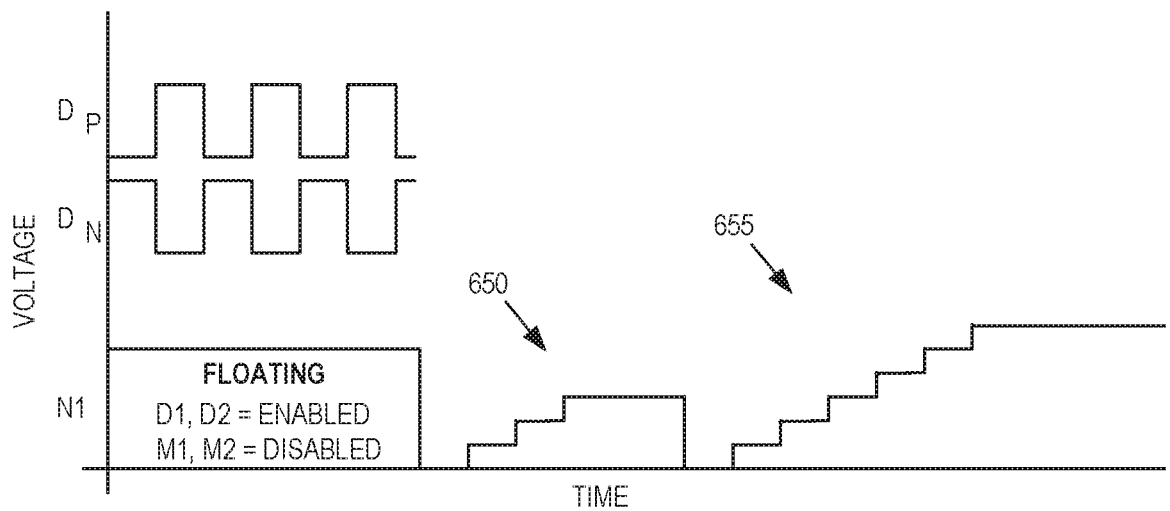
FIG. 6D is a chart illustrating voltage response curves generated by BIST circuitry while testing the health status of an adjustable lens, in accordance with an embodiment of the disclosure.

Impedance measurement circuit 603 is capable of measuring values indicative of both Rpar and Cpar of adjustable lens 130. In one embodiment, frequency generator 640 is implemented as a clock controller, which receives a control signal CTRL input from BIST control logic 405 for controlling its operation. Frequency generator 640 controls the nonoverlap switching of switches SW7 and SW8 within capacitive switch network 630 in much the same manner as frequency generator 640 to establish a voltage divider circuit with adjustable lens 130 to determine Rpar. However, instead of using a voltage comparator to monitor the voltage at circuit node N2, impedance measurement circuit 603 uses ADC 645 to convert (i.e., digitize) the voltage at circuit node N2 to a digital representation, which is then compared digitally by BIST control logic 405. Once a value for Rpar is determined, capacitive switch network 630 is used to sequentially transfer charge onto adjustable lens 130. As charge is transferred, the voltage on circuit node N2 is monitored by ADC 645. The voltage on circuit node N2 corresponds to the voltage across drive terminals DTp and DTn, which changes with each successive charge transfer. These sequential charge transfers create a voltage response curve at circuit node N2, which is also digitized by ADC 645 and analyzed by BIST control logic 405 to determine Cpar. In one embodiment, Cpar is determined based at least in part upon the curvature or rise time of one or more accumulated voltage response curves and the calculated value of Rpar. FIG. 6D is a chart illustrating two example voltage response curves 650 and 655 that are digitized by ADC 645 while testing adjustable lens 130 to determine Cpar. As illustrated, voltage response curve 650 is the result of three demonstrative charge transfers from capacitive switch network 630 to adjustable lens 130 via drive terminal DTn. Correspondingly, voltage response curve 655 is the result of six demonstrative charge transfers.

Figure 7:
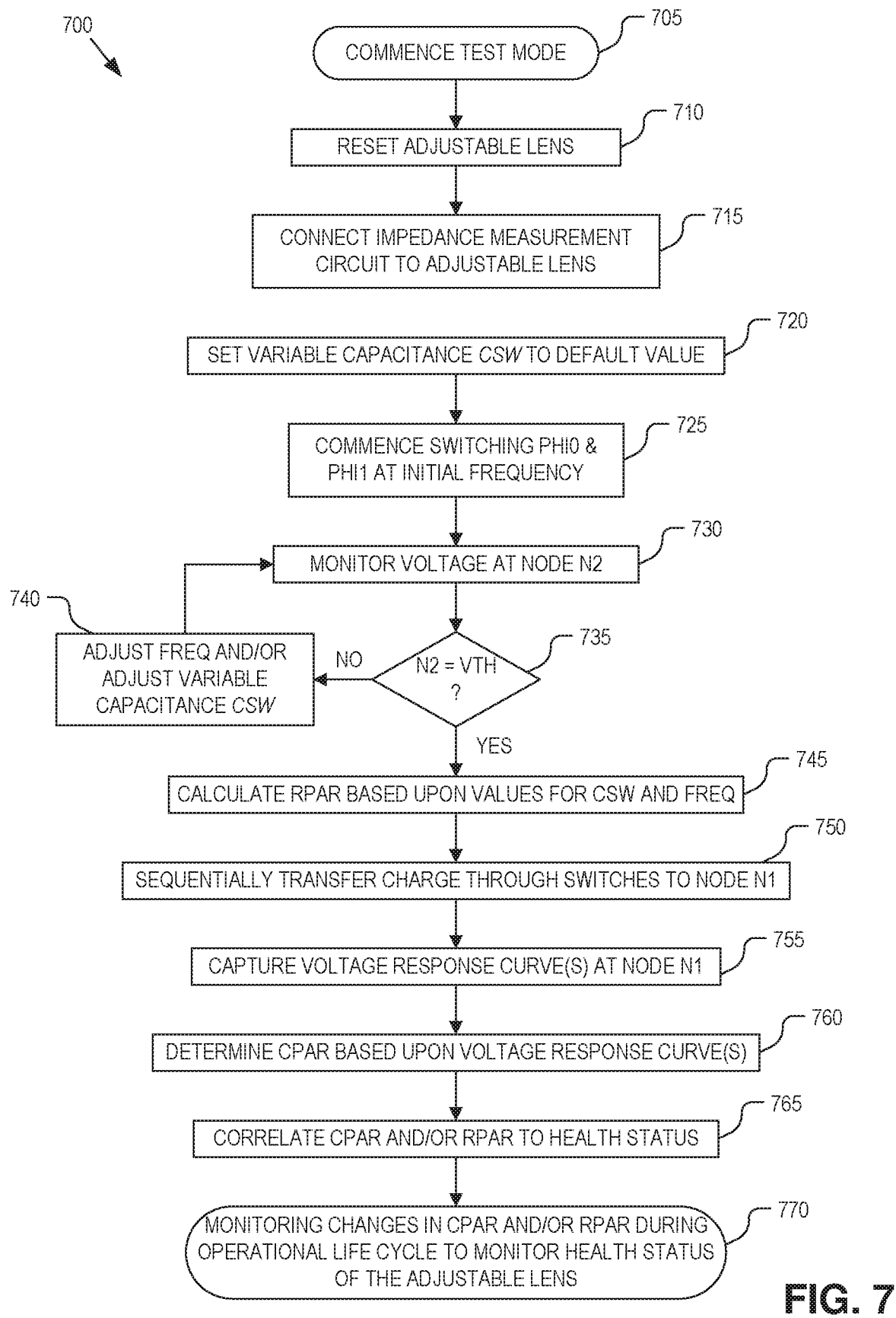
FIG. 7 is a flow chart illustrating a process of operation by BIST circuitry to test the health status of an adjustable lens, in accordance with an embodiment of the disclosure.

FIG. 7 is a flow chart illustrating a process 700 of operation by BIST circuitry 400 using impedance measurement circuit 603 to test the health status of adjustable lens 130, in accordance with an embodiment of the disclosure. Process 700 is explained with reference to both FIGS. 4 and 6. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

In a process block 705, ophthalmic device 100 enters a test mode of operation in preparation for measuring/monitoring the health status of adjustable lens 130. In a process block 710, adjustable lens 130 is reset. Resetting adjustable lens 130 may include asserting switches SW1 and SW2 (see FIG. 4) under the influence of BIST control logic 405 to apply default bias voltages VB1 and VB2 to drive terminals DTn and DTp. In other embodiments, only a single one of drive terminals DTn and DTp are biased. In yet other embodiments, the health status measurements may be executed while accommodation drivers Dp and Dn are driving adjustable lens 130 to a specific optical power setting. In other embodiments, BIST control logic 405 disconnects accommodation circuitry 175 during the test mode via switches SW5 and SW6.

In a process block 715, BIST control logic 405 (FIG. 4) connects impedance measurement circuit 410 (or 603) to drive terminals DTn and DTp of adjustable lens 130 via activation of switches SW3 and SW4, respectively. In process block 720, capacitance CSW of capacitor circuit 635 is set to a default value. The ability to change capacitance CSW provides a greater dynamic range for testing adjustable lens 130 over a larger range of Cpar and Rpar values with greater accuracy.

In a process block 725, frequency generator 640 begins toggling the switching signals PHI0 and PHI1 in a nonoverlapping manner at an initial frequency. This establishes a voltage divider circuit between Rpar of adjustable lens 130 and capacitance switch network 630. BIST control logic 405 monitors the voltage at circuit node N2 via its digitized representation output from ADC 645. The frequency of switching signals PHI0 and PHI1 is adjusted (process block 740) until the voltage at circuit node N2 reaches a threshold voltage Vth (e.g., Vth=Vs/2). Changing the frequency FREQ (or the capacitance CWS) changes the effective resistance of capacitive switch network 630. Once the voltage a circuit node N2 reaches the threshold voltage Vth (decision block 735), the digitized value DIG output from ADC 645 is used to calculate Rpar (process block 745). Rpar is calculated using the effective resistance Reff of capacitive switch network 630 and solving the voltage divider equation (2) for Rpar, $$V_{N2} = V_S \left( \frac{Rpar + Rp + Rn}{Reff + Rpar + Rp + Rn} \right) \quad (2)$$

where Rp and Rn are known resistances for drive terminals DTp and DTn, Reff is calculated based on equation 1 above, Vs is the source voltage in capacitive switch network 630, and Vn2 is the measured voltage at circuit node N2.

In process block 750, the sequential transfer of charge through switches SW7 and SW8 of capacitive switch network 630 is commenced to acquire voltage response curves (process block 755) at circuit node N2. The voltage response curves are also referred to as voltage response signatures. The curvature or voltage rise for a given amount or number of charge transfers is related to the values of Cpar and Rpar. Since Rpar has been measured, Cpar is determinable (process block 760) using RC circuit analysis.

Finally, in process block 765, the values of Rpar and Cpar are correlated to the health status of adjustable lens 130. If Rpar or Cpar are outside of expected ranges for Rpar and Cpar, then adjustable lens 130 may be determined to be defective. In process block 770, changes in Rpar and/or Cpar are monitored over time during the operational life cycle of ophthalmic device 100. The rate or magnitude of changes in Rpar and/or Cpar can also be correlated to the health status of adjustable lens 130. In one embodiment, Rpar and Cpar, along with changes in Rpar and Cpar, may be used to calculate an estimated remaining life span. In one embodiment, this estimation is executed external to ophthalmic device 100 by reader 105 or a device in communication with reader 105.

Figure 8A:
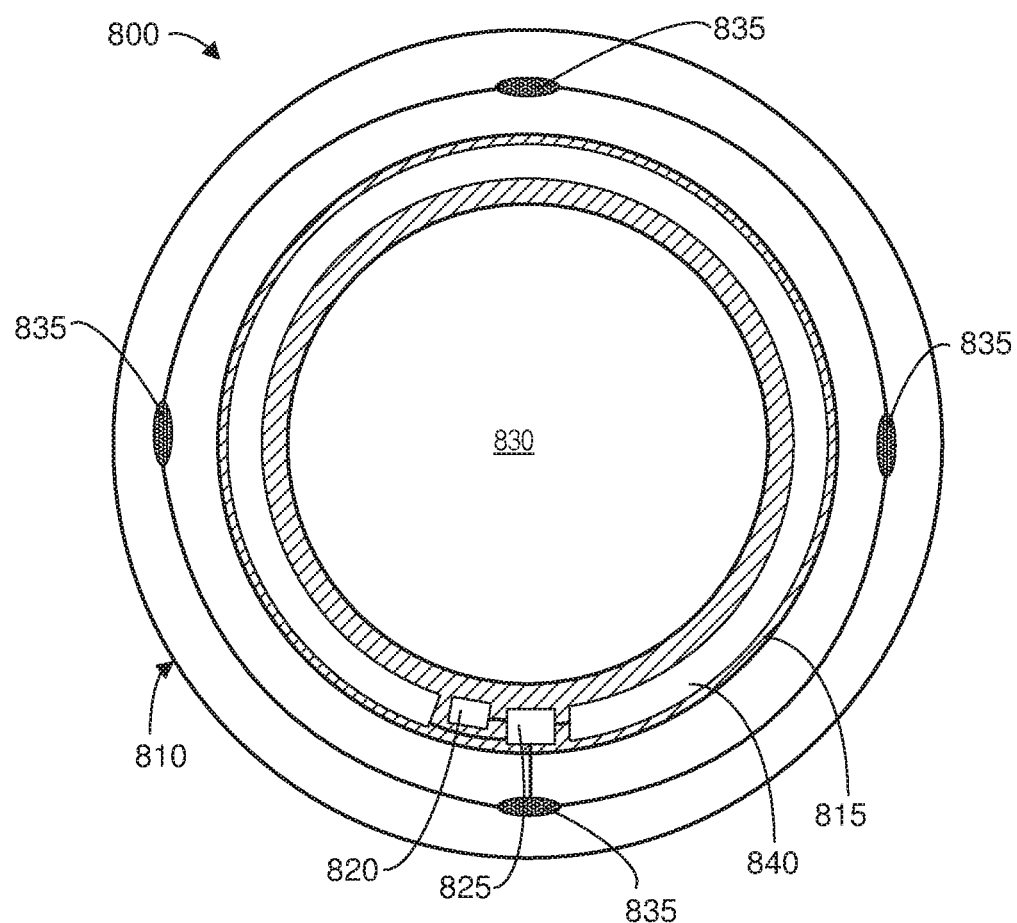
FIG. 8A is a top view illustration of a contact lens implementation of the ophthalmic device that includes BIST circuitry, in accordance with an embodiment of the disclosure.
Figure 8B:
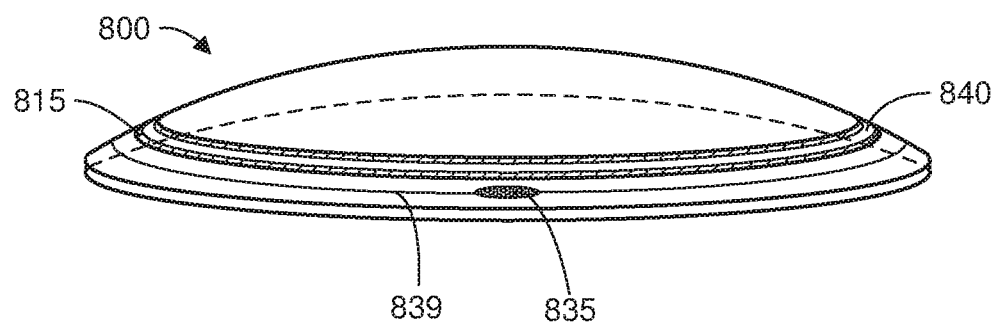
FIG. 8B is a perspective view illustration of the contact lens implementation of the ophthalmic device that includes BIST circuitry, in accordance with an embodiment of the disclosure.

FIG. 8A is a top view illustration of a smart contact lens 800, in accordance with an embodiment of the disclosure. FIG. 8B is a perspective view illustration of the same. Smart contact lens 800 is one possible form factor implementation of ophthalmic device 100. The illustrated embodiment of smart contact lens 800 includes an enclosure 810, a substrate 815, a power supply 820, a controller 825, an adjustable lens 830, a sensor system 835, and an antenna 840.

Enclosure 810 of smart contact lens 800 is shaped as a curved disk. As shown, to facilitate contact-mounting, the enclosure 810 can have a concave surface configured to adhere ("mount") to a moistened corneal surface (e.g., by capillary forces with a tear-film coating the corneal surface). Additionally, the smart contact lens 800 may be adhered by a vacuum force between the corneal surface and enclosure 810 due to the concave curvature. While mounted with the concave surface against the eye, the outward-facing surface of the enclosure 810 can have a convex curvature that is formed to not interfere with eye-lid motion while the smart contact lens 800 is mounted to the eye.

As illustrated, adjustable lens 830 (e.g., liquid crystal cell, electrowetting lens, MEMS lens, etc.) is disposed in the center region of smart contact lens 800 while the embedded electronics are disposed on the annular shaped substrate 815, which encircles a perimeter of adjustable lens 830. Enclosure 810 may be a substantially transparent material to allow incident light to be transmitted to the eye while smart contact lens 800 is mounted over the eye. Enclosure 810 may be a biocompatible material similar to those employed to form vision correction and/or cosmetic contact lenses in optometry, such as a polymeric material like polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise. Sensor system 835 is an impedance based system that measures the impedance of a user's tear film and correlates this value to gaze direction and/or an accommodation value for manipulating the accommodation setting of adjustable lens 830. Of course, other sensor systems (e.g., capacitive, inductive, photosensors, etc.) may be implemented for controlling auto-accommodation.

Figure 9:
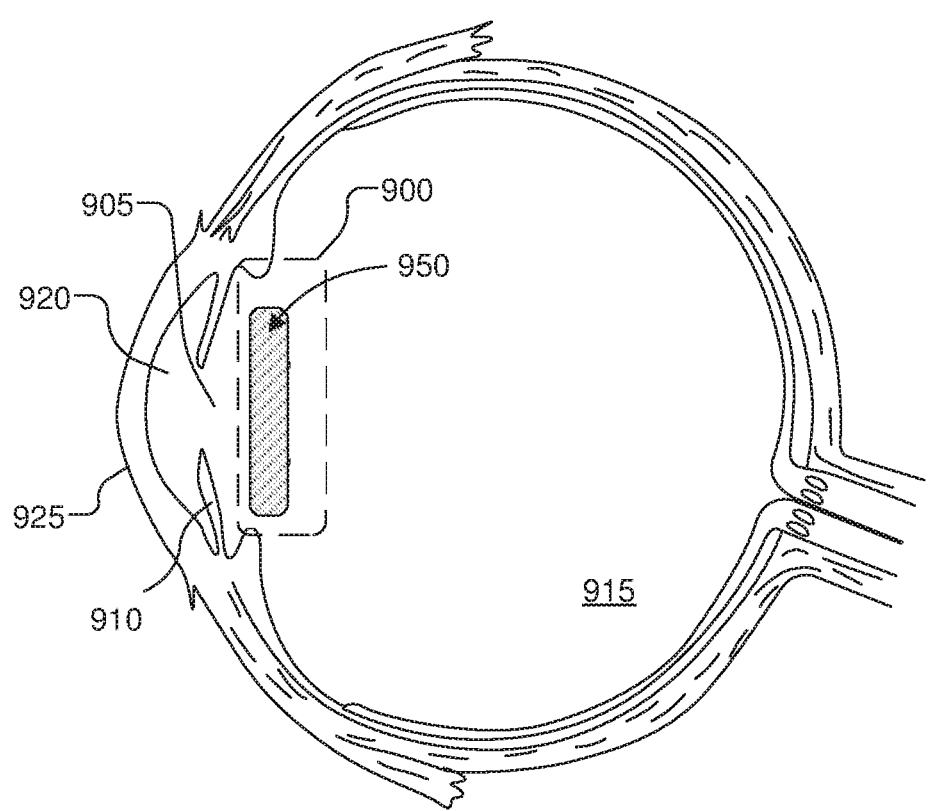
FIG. 9 is an illustration of an intraocular lens implementation of an ophthalmic device that includes BIST circuitry for testing an adjustable lens, in accordance with an embodiment of the disclosure.

FIG. 9 is a cross-sectional illustration of an intraocular lens 900, in accordance with an embodiment of the disclosure. Intraocular lens 900 is yet another possible form factor implementation of portions of ophthalmic device 100.

The illustrated embodiment of intraocular lens 900 includes a housing 950 and circuitry (e.g., adjustable lens 130, BIST circuitry 177, control logic 170) disposed therein. An exterior of intraocular lens 900 may include a surface of housing 950 that is biocompatible to accommodate direct contact with an interior of a human (or other) eye. Examples of such materials include, but are not limited to, any of various biocompatible hydrogels, silicones, hydrophobic acrylics, fluorinated polymethacrylates and/or the like.

Intraocular lens 900 may be implanted into the anterior chamber, the posterior chamber, or other locations of a user's eye. Intraocular lens 900 is illustrated as being implanted within the posterior chamber 905 behind an iris 910 of eye 915. However, intraocular lens 900 may be implanted into other locations, as well, such as anterior chamber 920 disposed between iris 910 and cornea 925.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one machine-accessible storage medium that provides instructions that, when executed by a machine, will cause the machine to perform operations comprising:

driving an adjustable lens disposed within an ophthalmic device via drive terminals coupled to the adjustable lens to change an optical power of the adjustable lens and provide adjustable accommodation to a user of the ophthalmic device;

connecting an impedance measurement circuit integrated into the ophthalmic device to the adjustable lens to measure data indicative of a health status of the adjustable lens, wherein the impedance measurement circuit is connected to the adjustable lens via the drive terminals used to change the optical power of the adjustable lens;

measuring an impedance of the adjustable lens across the drive terminals, which are used to change the optical power of the adjustable lens, with the impedance measurement circuit disposed within the ophthalmic device, wherein the impedance is measured via the drive terminals across the adjustable lens and the adjustable lens is an optical subcomponent of the ophthalmic device that changes optical power; and correlating the impedance to the health status of the adjustable lens, wherein the health status includes a determination that the adjustable lens is at least one of operational or defective based upon the impedance, wherein measuring the impedance of the adjustable lens comprises measuring both a parallel resistance of the adjustable lens and a parallel capacitance of the adjustable lens, and wherein correlating the impedance of the adjustable lens to the health status comprises correlating a combination of the parallel resistance and the parallel capacitance measured across the drive terminals to the health status of the adjustable lens.

2. The at least one machine-accessible storage medium of claim 1, wherein correlating the impedance to the health status of the adjustable lens comprises:

comparing the parallel resistance measured by the impedance measurement circuit to an expected resistance range; and determining that the health status of the adjustable lens is defective, if the parallel resistance falls outside the expected resistance range.

3. The at least one machine-accessible storage medium of claim 1, wherein correlating the impedance to the health status of the adjustable lens comprises:

comparing the parallel capacitance measured by the impedance measurement circuit to an expected capacitance range; and determining that the health status of the adjustable lens is defective, if the parallel capacitance falls outside the expected capacitance range.

4. The at least one machine-accessible storage medium of claim 1, wherein correlating the impedance to the health status of the adjustable lens comprises:

comparing the parallel resistance measured by the impedance measurement circuit to an expected resistance range;

comparing the parallel capacitance measured by the impedance measurement circuit to an expected capacitance range; and determining that the health status of the adjustable lens is acceptable, if the parallel resistance falls inside the expected resistance range and the parallel capacitance fall inside the expected capacitance range.

5. The at least one machine-accessible storage medium of claim 1, further providing instructions that, when executed by the machine, will cause the machine to perform further operations, comprising:

monitoring changes in at least one of the parallel resistance or the parallel capacitance measured by the impedance measurement circuit over time during an operational life cycle of the ophthalmic device; and determining the health status of the adjustable lens based at least in part upon the changes.

6. The at least one machine-accessible storage medium of claim 5, further providing instructions that, when executed by the machine, will cause the machine to perform further operations, comprising:

calculating an estimated remaining life span of the ophthalmic device based at least in part upon the changes in at least one of the parallel resistance or the parallel capacitance measured by the impedance measurement circuit, wherein the estimated remaining life span comprises a duration that the adjustable lens is expected to remain operational.

7. The at least one machine-accessible storage medium of claim 1, wherein measuring the parallel resistance of the adjustable lens comprises:

adjusting a switching frequency of a capacitive switch network to change an effective resistance of the capacitive switch network while the capacitive switch network is coupled to the adjustable lens;

monitoring a voltage of a circuit node disposed between the capacitive switch network and the adjustable lens, wherein the capacitive switch network and the adjustable lens form a voltage divider; and determining a resistance value indicative of the parallel resistance of the adjustable lens based upon the switching frequency and the voltage.

8. The at least one machine-accessible storage medium of claim 1, wherein measuring the parallel capacitance of the adjustable lens comprises:

sequentially transferring charge onto the adjustable lens;

monitoring changes in a voltage across the adjustable lens with each charge transfer to form a voltage response curve; and determining a capacitance value indicative of the parallel capacitance of the adjustable lens based upon the voltage response curve.

9. The at least one machine-accessible storage medium of claim 1, wherein the impedance of the adjustable lens is measured while the ophthalmic device is disposed in or on an eye of the user.

10. The at least one machine-accessible storage medium of claim 1, wherein the adjustable lens comprises one of a liquid crystal lens or an electrowetting lens, wherein the ophthalmic device comprises one of a contact lens that provides the adjustable accommodation or an intraocular lens that provides the adjustable accommodation, and wherein the impedance is an impedance across the liquid crystal lens or the electrowetting lens.

11. A method comprising:

driving an adjustable lens disposed within an ophthalmic device via drive terminals coupled to the adjustable lens to change an optical power of the adjustable lens and provide adjustable accommodation to a user of the ophthalmic device, wherein the adjustable lens is an optical subcomponent of the ophthalmic device that changes the optical power;

connecting an impedance measurement circuit integrated into the ophthalmic device to the adjustable lens to measure data indicative of a health status of the adjustable lens, wherein the impedance measurement circuit is connected to the adjustable lens via the drive terminals used to change the optical power of the adjustable lens;

measuring an impedance of the adjustable lens across the drive terminals, which are used to change the optical power of the adjustable lens, with the impedance measurement circuit disposed within the ophthalmic device; and correlating the impedance to the health status of the adjustable lens, wherein the health status includes a determination that the adjustable lens is at least one of operational or defective based upon the impedance, wherein measuring the impedance of the adjustable lens comprises measuring both the parallel resistance across the drive terminals coupled to the adjustable lens and the parallel capacitance across the drive terminals coupled to the adjustable lens, and wherein correlating the impedance of the adjustable lens to the health status comprises correlating both of the parallel resistance and the parallel capacitance measured across the drive terminals to the health status of the adjustable lens.

12. The method of claim 11, wherein correlating the impedance to the health status of the adjustable lens comprises:
comparing the parallel resistance measured by the impedance measurement circuit to an expected resistance range; and
determining that the health status of the adjustable lens is defective, if the parallel resistance falls outside the expected resistance range.

13. The method of claim 11, wherein correlating the impedance to the health status of the adjustable lens comprises:
comparing the parallel capacitance measured by the impedance measurement circuit to an expected capacitance range; and
determining that the health status of the adjustable lens is defective, if the parallel capacitance falls outside the expected capacitance range.

14. The method of claim 11, wherein correlating the impedance to the health status of the adjustable lens comprises:
comparing the parallel resistance measured by the impedance measurement circuit to an expected resistance range;
comparing the parallel capacitance measured by the impedance measurement circuit to an expected capacitance range; and
determining that the health status of the adjustable lens is acceptable, if the parallel resistance falls inside the expected resistance range and the parallel capacitance fall inside the expected capacitance range.

15. The method of claim 11, further comprising:
monitoring changes in at least one of the parallel resistance or the parallel capacitance measured by the impedance measurement circuit over time during an operational life cycle of the ophthalmic device; and
determining the health status of the adjustable lens based at least in part upon the changes.

16. The method of claim 15, further comprising:
calculating an estimated remaining life span of the ophthalmic device based at least in part upon the changes in at least one of the parallel resistance or the parallel capacitance measured by the impedance measurement circuit, wherein the estimated remaining life span comprises a duration that the adjustable lens is expected to remain operational.

17. The method of claim 11, wherein measuring the parallel resistance of the adjustable lens comprises:
adjusting a switching frequency of a capacitive switch network to change an effective resistance of the capacitive switch network while the capacitive switch network is coupled to the adjustable lens;
monitoring a voltage of a circuit node disposed between the capacitive switch network and the adjustable lens, wherein the capacitive switch network and the adjustable lens form a voltage divider; and
determining a resistance value indicative of the parallel resistance of the adjustable lens based upon the switching frequency and the voltage.

18. The method of claim 11, wherein measuring the parallel capacitance of the adjustable lens comprises:
sequentially transferring charge onto the adjustable lens;
monitoring changes in a voltage across the adjustable lens with each charge transfer to form a voltage response curve; and
determining a capacitance value indicative of the parallel capacitance of the adjustable lens based upon the voltage response curve.

19. The method of claim 11, wherein the impedance of the adjustable lens is measured while the ophthalmic device is disposed in or on an eye of the user.

20. The method of claim 11, wherein the adjustable lens comprises one of a liquid crystal lens, an electrowetting lens, or a microelectromechanical system (MEMS) lens, wherein the ophthalmic device comprises one of a contact lens that provides the adjustable accommodation or an intraocular lens that provides the adjustable accommodation, and wherein the impedance is an impedance across the liquid crystal lens, the electrowetting lens, or the MEMS lens.

* * * * *